United States Patent [19]

Warnke et al.

[11] 4,355,233
[45] Oct. 19, 1982

[54] METHOD AND APPARATUS FOR NEGATING MEASUREMENT EFFECTS OF INTERFERENT GASES IN NON-DISPERSIVE INFRARED ANALYZERS

[75] Inventors: Dale F. Warnke, Irvine; Carl N. Cederstrand, Brea; Charles A. Keenan, Irvine, all of Calif.

[73] Assignee: Beckman Instruments, Inc., Fullerton, Calif.

[21] Appl. No.: 117,175

[22] Filed: Jan. 31, 1980

Related U.S. Application Data

[63] Continuation of Ser. No. 13,945, Feb. 22, 1979, abandoned.

[51] Int. Cl.³ .............................................. G01J 1/00
[52] U.S. Cl. .................................. 250/343; 250/345
[58] Field of Search ............... 250/343, 344, 345, 339, 250/340, 373

[56] References Cited

U.S. PATENT DOCUMENTS 3,770,974 11/1973 Fertig .................................. 250/344
3,925,667 12/1975 Staab .................................. 250/343
4,204,768 5/1980 N'Guyen ........................... 250/343

OTHER PUBLICATIONS

Proceedings of the Society of Photo-Optical Instrumentation Engineers, "A Multigas Analyzer for Automobile Exhausts", Pembrook et al., Aug. 26-27, 1976, vol. 95, pp. 84-91.
Environmental Science & Technology, "Unique Ambient CO Monitor Based on Gas Filter Correlation: Performance & App.", Chaney et al., vol. 11, No. 13, Dec. '77, pp. 1185-1190.
Horiba Model A1A-21-AS Gas Analyzer.

Primary Examiner—Alfred E. Smith
Assistant Examiner—Janice A. Howell
Attorney, Agent, or Firm—Robert J. Steinmeyer; P. R. Harder; E. C. Jason

[57] ABSTRACT

A method and apparatus is disclosed for selectively determining by non-dispersive infrared techniques the concentration of a gaseous constituent in a sample gas mixture while determining and discounting deleterious effects of spectrally interfering gases in the sample gas mixture.

17 Claims, 5 Drawing Figures

○ BACKGROUND GAS INERT TO INFRARED RADIATION
● CARBON MONOXIDE OR CONSTITUENT DESIRED TO BE ACCURATELY KNOWN
⦁ INTERFERENT GAS
▭ INFRARED RADIATION BEAM

O  BACKGROUND GAS INERT TO INFRARED RADIATION

•  CARBON MONOXIDE OR CONSTITUENT DESIRED
   TO BE ACCURATELY KNOWN

·  INTERFERENT GAS

▭  INFRARED RADIATION BEAM

- ○ BACKGROUND GAS INERT TO INFRARED RADIATION
- ● CARBON MONOXIDE OR CONSTITUENT DESIRED TO BE ACCURATELY KNOWN
- • INTERFERENT GAS
- ▭ INFRARED RADIATION BEAM

METHOD AND APPARATUS FOR NEGATING MEASUREMENT EFFECTS OF INTERFERENT GASES IN NON-DISPERSIVE INFRARED ANALYZERS

CROSS-REFERENCE TO RELATED APPLICATIONS

The present application is a continuation of prior copending application Ser. No. 13,945, filed Feb. 22, 1979, now abandoned.

BACKGROUND OF THE INVENTION

The present invention relates to a method and apparatus for increasing accuracy in non-dispersive infrared analyzer systems for determining the concentration of a preselected gas in a homogeneous sample gas of spectrally overlapping constituents, and more particularly to a method and apparatus for determining the concentration of an interferent gas and removing its effect on the measurement of a preselected constituent gas in a gas sample.

Prior art has disclosed many methods and apparatus for measuring concentration content of a preselected component in a sample gas, the most spectrally specific of which is a non-dispersive infrared analyzer utilizing a pneumatic detector.

While pneumatic detectors charged with the component of interest will give generally accurate indications of the concentration of the selected component, a problem is many times encountered where other gas components present in the sample stream have absorption bands which either overlap or lie within the major absorption band of the selected components. For example, carbon dioxide has an infrared absorption band which overlaps the major infrared absorption band of carbon monoxide while water vapor has a minor absorption band which lies within the major absorption band of carbon monoxide. Thus, these gases, when present, interfere with the measurement of carbon monoxide by non-dispersive infrared techniques. In order to compensate for the infrared energy absorbed by water vapor and carbon dioxide, prior art has used additional pneumatic detectors specifically sensitized to determine the concentration of carbon dioxide and/or water vapor and in turn subtract the effect of these concentrations from the concentration measured by the carbon monoxide detector. This solution to the problem results in a very complex, bulky, and expensive carbon monoxide detectors for testing the sample gas. In order to accurately measure the concentration of a gas such as carbon monoxide, an additional pneumatic detector is required for each interferent to be measured, resulting in a multiple in the cost of a detector to measure one gas.

It is therefore an object of the present invention to provide a simple dual beam, non-dispersive infrared analyzer utilizing a single pneumatic detector which measures the component concentration in a sample gas with increased accuracy.

It is another object of the present invention to provide an inexpensive accurate measurement of a component gas in a sample gas stream.

It is a further object of the present invention to provide a gas concentration analyzer which has a high degree of accuracy.

SUMMARY OF THE INVENTION

The foregoing objects are satisfied and the foregoing deficiencies are overcome by the present invention which comprises solid state detectors disposed within the sample cell of a dual-beam, non-dispersive infrared analyzer utilizing a pneumatic detector. These solid state detectors are situated behind narrow band filters which pass infrared radiation of a wavelength corresponding to the wavelength of interfering species which is different from the wavelength of the infrared waves absorbed by the constituent gas to be measured. The energy incident upon the solid state detectors is converted into an electrical signal. This signal is processed further to represent concentration of interferent gases. The processed signal is algebraically combined with the signal produced by the pneumatic detector. The resulting signal is an indication of the concentration of a preselected constituent of a sample gas without the inaccuracies introduced by interferent gases.

DESCRIPTION OF THE PREFERRED EMBODIMENT

Figure 1:
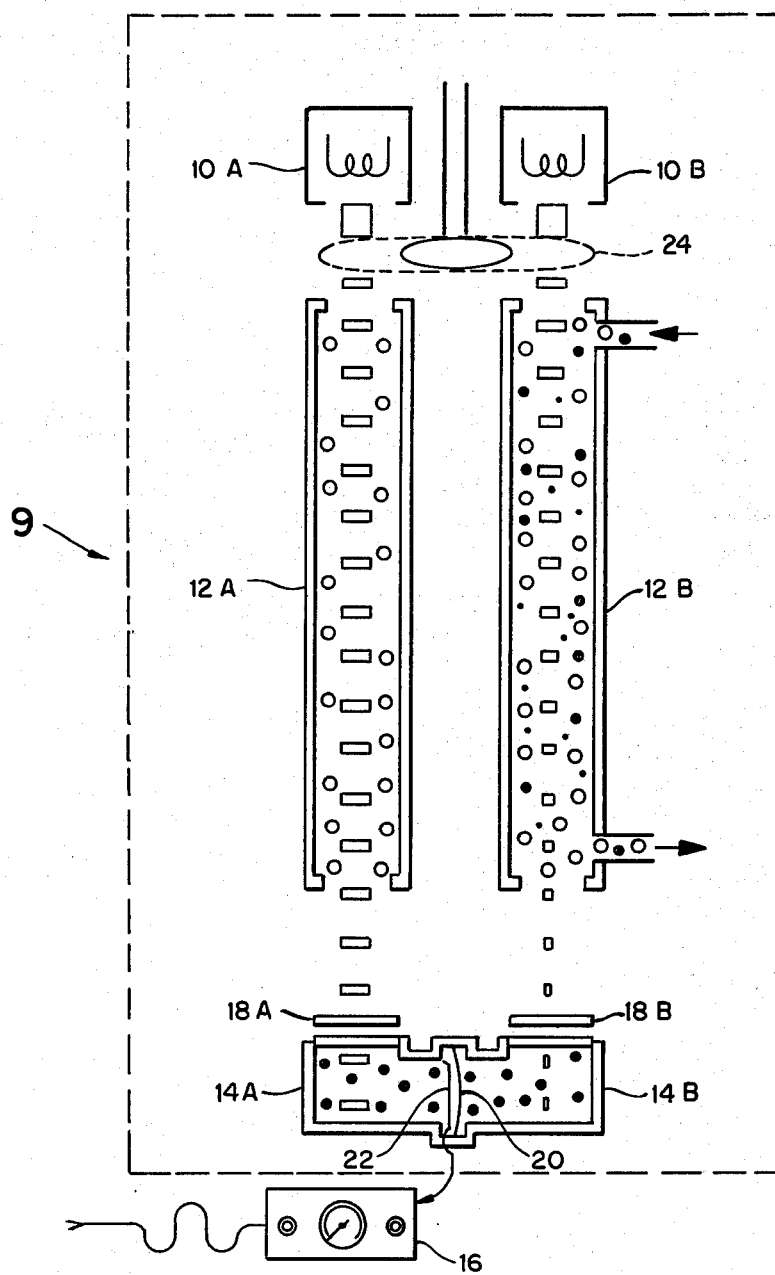
FIG. 1 illustrates a prior art dual beam non-dispersive infrared analyzer utilizing a pneumatic detector.

FIG. 1 illustrates a prior art dual beam non-dispersive infrared analyzer 9 comprising infrared sources 10A and 10B, a reference cell 12A, a sample cell 12B, a pneumatic detector having chambers 14A and 14B, indicator 16 and narrow band filters 18A and 18B.

Narrow band filters 18A and 18B are not essential but are recommended to provide an improved measurement of a constituent gas by limiting the number of spectrally interferring species to gases which have absorption bands within the bandwidth of the filters. Therefore, narrow band filters 18A and 18B are included as part of the non-dispersive infrared analyzer with which the present invention is used. However, it is understood by one skilled in the art that narrow band filters 18A and 18B are not essential.

In practice, reference cell 12A is filled with an inert gas or may be evacuated, the essential characteristic being that the contents of reference cell 12A contains a gas which does not absorb infrared energy or a gas for which the infrared energy absorption remains constant for the specific application of interest. The sample gas stream containing the component gas to be measured flows through the sample cell 12B. Two reasonably matched narrow band filters 18A and 18B are located in front of pneumatic detector chambers 14A and 14B to pass a narrow band of infrared radiation which corresponds with a strong absorption band of the constituent gas to be measured. Narrow band filters 18A and 18B may be of any type commercially available. However, interference filters on sapphire substrates are preferred. The narrow band filters cover detector windows which are in line with reference cell 12A and sample cell 12B. Detector chambers 14A and 14B are generally filled with the same kind of gas as that to be measured, in this case carbon monoxide, and are separated by a diaphragm 20. Diaphragm 20 is a very thin sheet of some conductive material such as aluminum foil which serves as the variable plate of a capacitor. Disposed next to diaphragm 20 is an electrode 22 which serves as the fixed plate of a capacitor.

Figure 3:
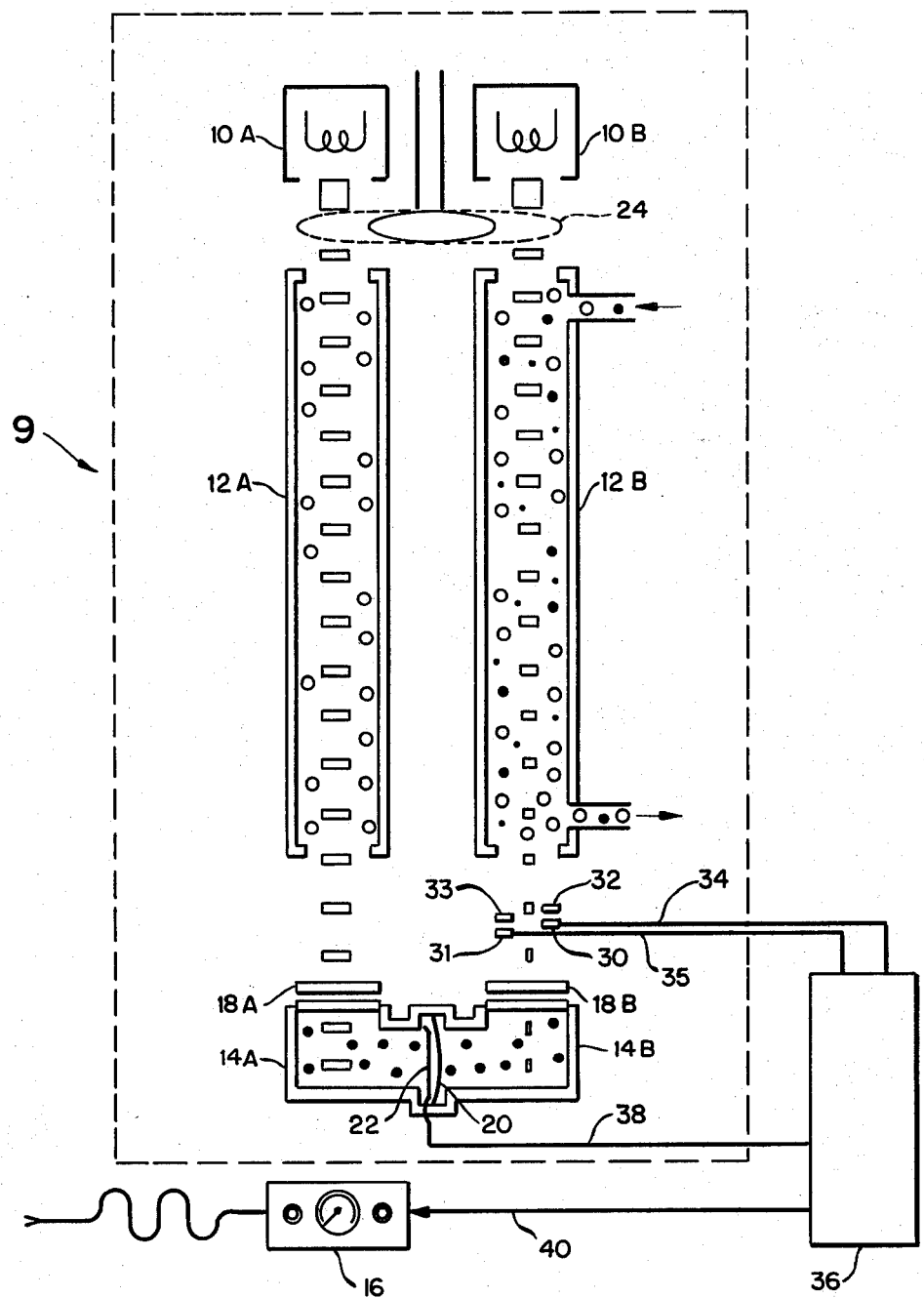
FIG. 3 illustrates a dual beam, non-dispersive analyzer constructed in accordance with the teachings of the present invention.

In operation, infrared sources 10A and 10B emit a wide spectrum of infrared radiation. A rotating chopper blade 24 is operated to interrupt the infrared sources 10A and 10B simultaneously, preferably at about ten times per second. The action of chopper blade 24 produces pulsating infrared radiation which travels synchronously through reference cell 12A and sample cell 12B. A broad band of infrared energy, including that which is characteristic of the component gas to be measured, in this case carbon monoxide, travels down reference cell 12A and is incident upon narrow band filter 18A. Narrow band interference filter 18A transmits only those wavelengths which coincide with the absorption band of the constituent gas to be measured, such as the 4.7 micron absorption band of carbon monoxide. Inside pneumatic detector reference chamber 14A, a proportional amount of the infrared radiation is absorbed by the carbon monoxide contained therein and produces a heating effect. The infrared energy from source 10B similarly travel down sample cell 12B. However, the infrared radiation transmitted to chamber 14B will be diminished by absorption by any carbon monoxide which may be present in sample cell 12B as illustrated in FIGS. 1 and 3. Infrared energy within the absorption bandwidth, characteristic of carbon monoxide, which has not been absorbed by the component gas in sample cell 12B will be absorbed proportionately by the carbon monoxide a pneumatic detector chamber 14B. The carbon monoxide in pneumatic detector chamber 14A will heat to a greater extent than that in pneumatic detector chamber 14B since an amount of the infrared energy has been absorbed by carbon monoxide contained in sample cell 12B. The unequal heating in pneumatic detector chambers 14A and 14B will produce a pressure difference, causing deflection of diaphragm 20 which in turn will change the capacitance established between electrode 22 and disphragm 20. Indicator 16, which in essence measures this change in capacitance between electrode 22 and disphragm 20, will indicate the concentration of the component gas, carbon monoxide.

Figure 2:
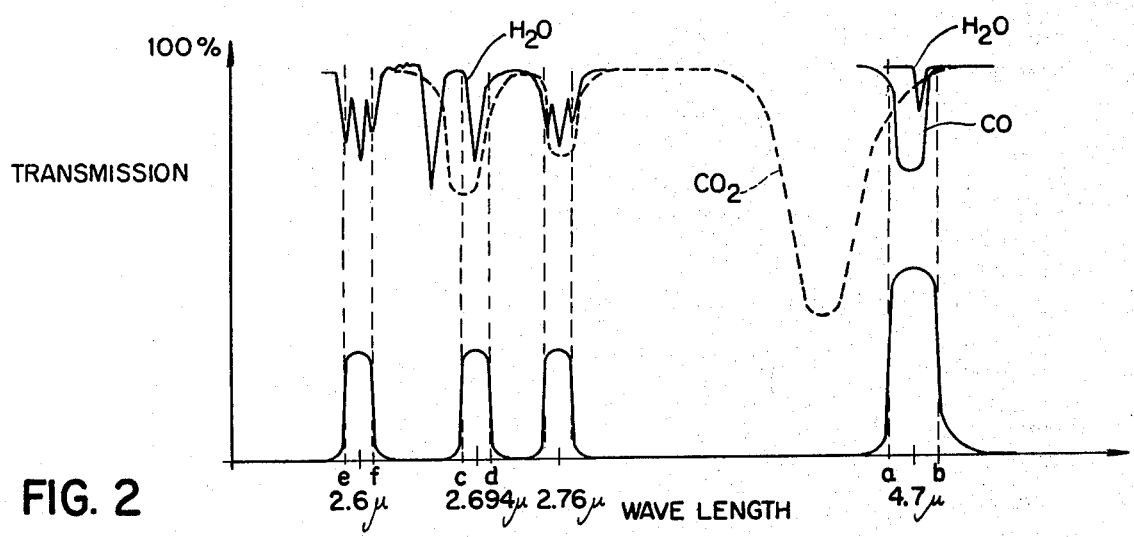
FIG. 2 illustrates the bands of infrared radiation absorbed by several gases of interest.

Referring now to FIG. 2, a graph representing the infrared spectrum, portions of which are absorbed by carbon monoxide, carbon dioxide and water vapor, is illustrated. Carbon dioxide absorption bands are indicated by the dotted lines marked "$CO_2$". Water vapor absorption band are indicated by the spiked solid lines marked "$H_2O$". Carbon monoxide absorption bands are indicated by the solid line marked "CO". Bandwidths illustrated as having center points at 2.6 microns, 2.694 microns (2.7 microns), 2.76 microns and 4.7 microns are representative of optical filters which may be used with the present invention. Absorption by carbon monoxide, carbon dioxide and water vapor can be seen on the graph between points a and b. Carbon monoxide will absorb infrared radiation within a narrow bandwidth having its center at 4.7 microns. However, also at this bandwidth, carbon dioxide and water vapor will weakly absorb some of the infrared energy. Between points "c" and "d", having its center at 2.694 microns, carbon dioxide and water vapor are strong absorbers whereas carbon monoxide is essentially a non-absorber of infrared energy. Between points "e" and "f", having its center at 2.6 microns, water vapor is a strong absorber while carbon monoxide and carbon dioxide are negligible absorbers of infrared energy. Hence, water vapor may be independently measured at wavelengths centered at 2.6 microns and an independent measurement of carbon dioxide may be obtained by subtracting the effect of water vapor measured at 2.6 microns from the measurement of carbon dioxide and water vapor measured at 2.7 microns. Although measurements of water vapor at 2.6 microns and water vapor and carbon dioxide at 2.7 microns are preferred, carbon dioxide and water vapor are also absorbers of infrared energy in a bandwidth having its center at 2.76 microns in addition to the one centered at 2.7 microns where carbon monoxide is again essentially a non-absorber. Thus, the measurement of the concentration of carbon monoxide will also include trace amounts of carbon dioxide and water vapor (carbon monoxide measurement error) whereas the concentration of water vapor and carbon dioxide can be measured without absorption of infrared radiation by carbon monoxide.

Referring now to FIG. 3, a non-dispersive infrared analyzer is illustrated constructed in accordance with the teaching of the present invention. Portions of the analyzer of FIG. 3 which are identical to the analyzer of FIG. 1 have identical numbers and will not be described further. Solid state detectors 30 and 31 are illustrated as being disposed within sample cell 12B and having optical filters 32 and 33 in front thereof and conductors 34 and 35 leading to electronic circuit 36, respectively. Solid state detectors 30 and 31 may be either thermistors, lead sulfide sensors, lead selenide sensors, pyroelectric devices or any solid state black body detector. Pyroelectric devices are preferred due to their sensitivity and low cost. Optical filters 32 and 33 may be of any type commerically available. However, narrow band, interference type infrared filters on a quartz substrate are preferred. Filters 32 and 33 may have a bandwidth center point of any value which coincides with the absorption band of the interferent gases. In the case where carbon monoxide is to be determined in the presence of water vapor and carbon dioxide, optical filter 32 preferably has a bandwidth of 0.05 microns with a center point at 2.6 microns. Optical filter 33 preferably has a bandwidth of 0.03 microns with its center point of 2.694 microns although a bandwidth of 0.04 microns with its center point at 2.76 microns is equally suitable. Electronic circuit 36 also receives an input from diaphragm 20 through conductor 38 and issues an output to indicator 16 through conductor 40.

Infrared radiation in the 2.6 and 2.694 micron regions, the preferred center point for the bandwidths passed by the optical filters 32 and 33, respectively, travels down sample gas channel 12B and is partially absorbed by any carbon dioxide and/or water vapor contained in the sample gas. The portion of the infrared energy not absorbed by water vapor or carbon dioxide will be passed by optical filters 32 and 33 to solid state detectors 30 and 31, respectively. The energy from the passed infrared radiation will cause a signal to be produced by solid state detectors 30 and 31. The signals produced by solid state detectors 30 and 31 are, respectively, related to the concentration of water vapor alone and water vapor and carbon dioxide in the sample gas being tested. The infrared radiation within the principal absorption bandwidth of the component gas being analyzed, in this case carbon monoxide, will not pass through optical filters 32 and 33. Infrared radiation within the abosrption bandwidth of carbon monoxide will pass narrow band filter 18B and be absorbed by the carbon monoxide contained within pneumatic detector chamber 14B. The infrared radiation within the absorption bandwidth of carbon monoxide centered at 4.7 microns does not affect the output of the solid state detectors 30 and 31 and the infrared radiation within the absorption bandwidth of carbon dioxide and water vapor centered at 2.6 and 2.7 microns does not affect the output of pneumatic detector 14. The operation of the non-dispersive infrared analyzer 9 remains essentially unchanged from its operation in prior art. The signals, however, produced by pneumatic detector 14 and solid state detectors 30 and 31 are further processed through electronic circuit 36 prior to display at indicator 16.

Figure 4:
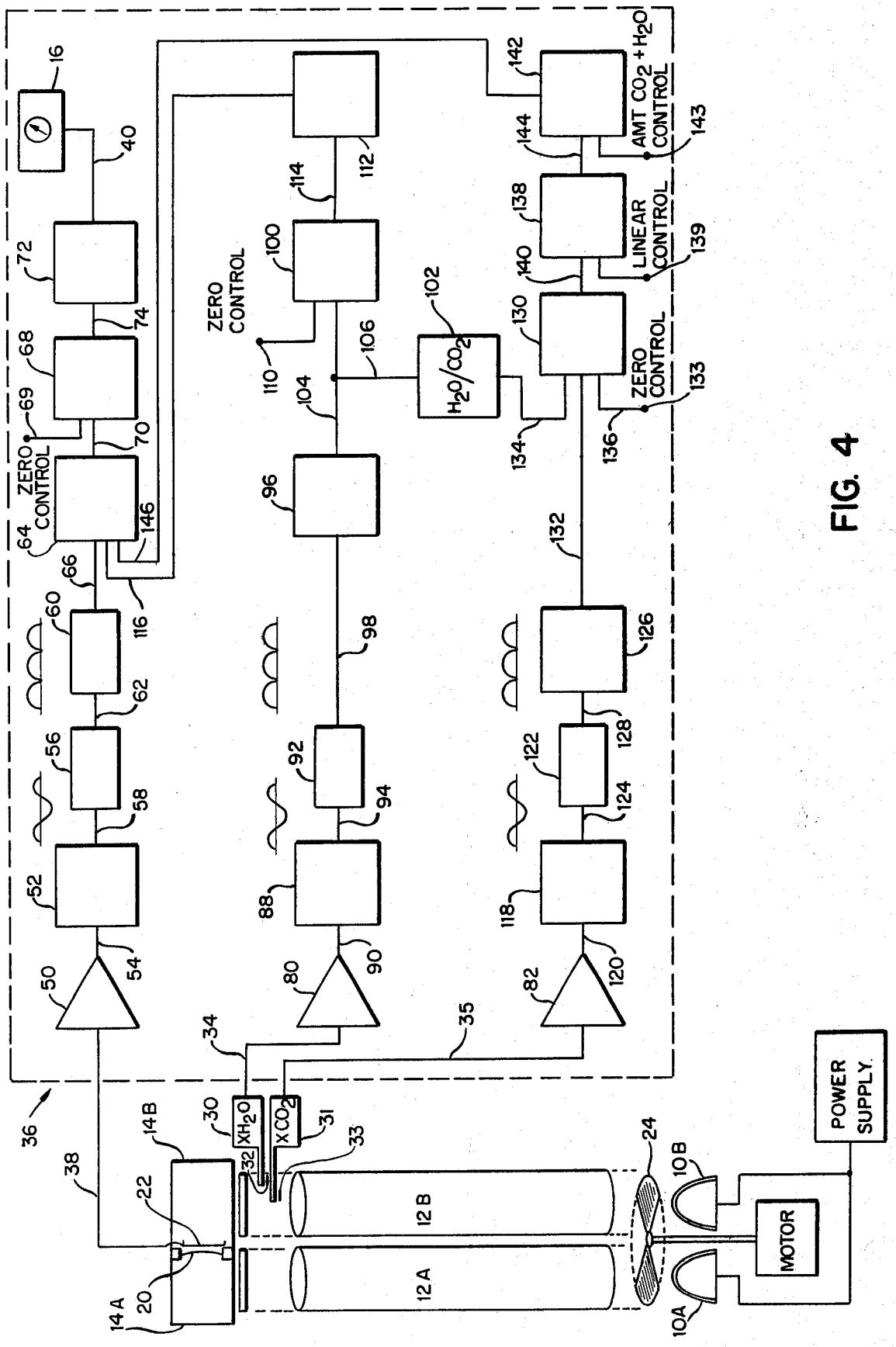
FIG. 4 is a block diagram of the electronic circuitry of the present invention.

FIG. 4 illustrates electronic circuit 36 in block form as comprising a charge detector and amplifier 50 connected to electrode 22 through conductor 38 on its input side and its output connected to chop frequency bandpass filter 52 through conductor 54. The output of chop frequency bandpass filter 52 is connected to the input of demodulator 56 through conductor 58. Demodulator 56 is connected to filter 60 through conductor 62. Filter 60 is connected to summing circuit 64 through conductor 66 which is connected to scaling amplifier 68, through conductor 70. Scaling amplifier 68 has a zero control 69 and is connected to low pass filter 72 through conductor 74 which is connected to carbon monoxide display unit 16 through conductor 40. Electronic circuit 36 also comprises amplifiers 80 and 82 having their inputs connected to solid state detectors 30 and 31 through conductors 34 and 35, respectively. Amplifier 80 is connected to chop frequency bandpass filter 88 through conductor 90 which is connected to demodulator 92 through conductor 94. Demodulator 92 is connected through conductor 98 to low pass filter 96 which is connected to summing amplifier 100 and H$_2$O/CO$_2$ control 102 through conductors 104 and 106, respectively. Summing amplifier 100 receives an additional input from zero control 110 and produces an output to H$_2$O control 112 through conductor 114. H$_2$O control 112 produces an output which is the second input to summing circuit 64 through conductor 116.

The amplifier 82 is connected through conductor 120 to chop frequency bandpass filter 118 which is connected to demodulator 122 through conductor 124. Demodulator 122 is connected through conductor 128 to low pass filter 126 which furnishes one input to summing amplifier 130 through conductor 132. Summing amplifier 130 receives an input from H$_2$O/CO$_2$ control 102 and zero control 133 through conductors 134 and 136, respectively. Summing amplifier 130 produces the input to linearization circuit 138 through conductor 140. Linearization circuit 138, having linear control 139, supplies the input to CO$_2$ control 142 through conductor 144. CO$_2$ control 142 has a CO$_2$+H$_2$O control 143 and supplies the third input to summing circuit 64 through conductor 146. Although electronic circuit 36 is illustrated as comprising discrete components, it is understood by one skilled in the art that many variations are possible and the functions of electronic circuit 36 may be accomplished by a microprocessor or the like.

In operation, charge detector 50 receives an indication of capacitance through conductor 38 from electrode 22. This signal will be an a.c. signal which is fed to chop frequency bandpass filter 52 which removes spurious a.c. signals and feeds a clean a.c. signal having the frequency determined by chopper 24, preferably 10 hertz, to demodulator 56. Demodulator 56 functions as a full wave rectifier and will feed a d.c. signal with an a.c. ripple to filter 60. Filter 60 smooths out the d.c. signal with a 10 Hz ripple so that summing circuit 64 receives a smooth d.c. signal through conductor 66. Thus, the signal on conductor 66 into summing circuit 64 is a pure d.c. signal whose amplitude is proportional to the concentration of the constituent gas of interest (in the example, carbon monoxide) plus the concentration of any interferent gases having absorption bands in the same wavelength region being utilized to detect the constituent gas (in the example, carbon dioxide and water vapor).

Amplifier 80 receives an a.c. signal from solid state detector 30 through conductor 34. This a.c. signal is amplified and fed to chopper frequency bandpass filter 88. Chopper frequency bandpass filter 88 removes all spurious a.c. signals to produce a 10 Hz a.c. signal, the frequency of chopper blade 24, to demodulator 92. Demodulator 92 serves the same furnction as demodulator 56, that is to produce a full wave rectified a.c. signal to filter 96 which smooths the d.c. with the a.c. ripple into a pure d.c. signal. The d.c. signal from filter 96 is fed to summing amplifier 100 where it is combined with a d.c. signal from zero control 110. The d.c. signal from filter 96 is also fed through the H$_2$O/CO$_2$ control 102 to summing amplifier 130 which will be described in detail later. Summing amplifier 100 produces a signal to H$_2$O control 112 which further processes the signal and inverts the signal to assure a signal with opposite polarity to that fed to summing circuit 64 from filter 60. The signal on conductor 116 to summing amplifier 64 is a pure d.c. signal having an amplitude proportional to the concentration of water vapor in the sample gas. Amplifier 82 receives the signal from solid state detector 31 and amplifies this input to produce a signal to chopper frequency bandpass filter 118 which serves the same function as filters 88 and 52, that is to remove spurious a.c. signals from the desired 10 hertz signal. The clean a.c. signal is then fed to demodulator 122, which acts as a fully wave rectifier, to produce a d.c. with an a.c. ripple to filter 126 which removes the ripple and produces a smooth d.c. signal to summing amplifier 130. Summing amplifier 130 receives a portion of the signal from filter 96 through H$_2$O/CO$_2$ control 102 and the d.c. input from zero control 133. CO$_2$/H$_2$O control 102 provides a signal to correct for any water vapor absorption which may affect the signal produced by solid state detector 31. Summing amplifier 130 combines these three signals and produces an output to linearization circuit 138. Linearization circuit 138 linearizes the signal from summing amplifier 130 to assure a linear relationship between the signal from carbon dioxide sensor 31 and the error in the carbon monoxide measurement signal from conductor 66 due to the amount of carbon dioxide present in the gas sample (see FIG. 5). Amplifier 142 has a gain adjustment which supplies the required amount of signal from linearization circuit 138 necessary to match the carbon monoxide signal from conductor 66 due to carbon dioxide in the test sample. Amplifier 142 also inverts this signal to again assure a signal of opposite polarity to that produced by filter 60 and feeds this inverted signal to summing circuit 64 where it is combined with the d.c. signals indicating the amount of carbon monoxide and the amount of water vapor in the sample. The signal from summing circuit 64 is fed through scaling amplifier 68 which sets up the proportional relationship between the amount of carbon monoxide in the sample and the voltage of the combined signals from conductors 66, 116, and 146. The signal from scaling amplifier 68 is passed through low pass filter 72 to remove any remanent spurious a.c. signals and feeds this signal to carbon monoxide display 16 wherein the amount of carbon monoxide in the sample is indicated.

Figure 5:
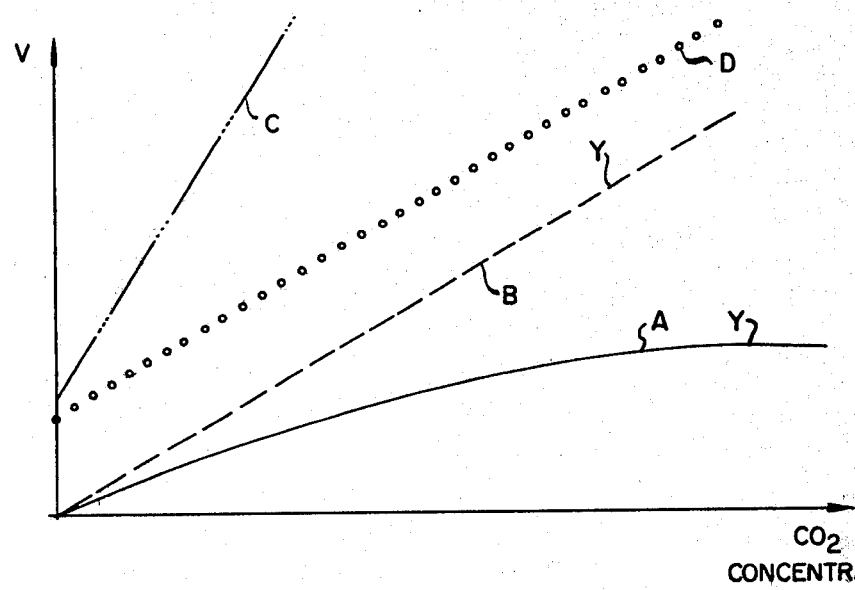
FIG. 5 is a graphical representation of concentration versus potential for a linearized and a nonlinearized measuring instrument.

FIG. 5 is a graphical representation of carbon dioxide concentration versus voltage in a test sample. Solid curve A represents the detected relationship between carbon dioxide concentration and voltage from the solid state detector 31, as seen at the output of summing amplifier 130. Dashed line B represents the linear relationship between carbon dioxide concentration and voltage from linearization circuit 138 which may be any suitable linearization circuit known in the art. Both lines A and B are for zero water vapor content. Broken line C represents the relationship of the output of linearization circuit 138 and the carbon dioxide content with a constant amount of water vapor content without the signal from the $H_2O/CO_2$ control 102 through conductor 134. Dotted line D represents the relationship of the output of linearization circuit 138 and the carbon dioxide content with a constant amount of water vapor content with the signal from the $H_2O/CO_2$ control 102 through conductor 134 and with control 102 adjusted such that the response to water vapor is the same with or without carbon dioxide present. The voltage produced by sensor 31 does not have a linear relationship with the carbon monoxide measurement signal at conductor 66 due to the presence of carbon dioxide in the test sample and thus the linearization circuit 138 is used to improve the capability to remove the error due to carbon dioxide. Once the voltage from sensor 31 is linearized at conductor 144, the response is essentially linear with either carbon dioxide or water vapor, when only one of the two are present. However, without the $H_2O/CO_2$ control and the water vapor signal on conductor 134, a linear relationship between the carbon monoxide measurement error and the response at conductor 144 due to carbon dioxide and water vapor when both are present in varying amounts is essentially limited in range. The control 102 is adjusted to remove some of the water vapor signal such that the response at conductor 144 is linear for an appreciable range of variation for carbon dioxide and water vapor when both are present to the carbon monoxide measurement error signal at conductor 66 due to carbon dioxide and water vapor.

The voltage produced by sensor 30 is essentially linear with the water vapor content and thus does not need a linearization circuit for the most general application.

As was indicated previously, pneumatic detector 14 will produce a signal indicative of the carbon monoxide content in the sample gas; however, this signal will also contain inaccuracies due to carbon dioxide and water vapor which will absorb infrared energy within the same bandwidth as carbon monoxide (see FIG. 2). Solid state detector 30, on the other hand, will produce a signal indicative of the amount of water vapor in the sample since optical filter 32 has its bandwidth centered at 2.595 microns (2.6 microns) with a preferred bandwidth of 0.05 microns. The signal from solid state sensor 31 will produce a signal indicative of the carbon dioxide in the sample and also an amount of water vapor in the sample since optical filter 33 has its bandwidth center at 2.692 microns with a preferred bandwidth of 0.03 microns, although an alternate center point of 2.764 microns with a preferred bandwidth of 0.04 microns may be used. Summing circuit 64 will receive an indication of the carbon monoxide plus carbon dioxide and water vapor present in the sample from pneumatic detector 14 and will receive a signal representative of the water vapor in the sample from solid state detector 30 and a signal representative of the carbon dioxide and water vapor in the sample from solid state detector 31. The signal from pneumatic detector 14 is positive, whereas the signal from solid state detectors 30 and 31, after processing by electronic circuit 36, are negative so that the amount of carbon monoxide plus carbon dioxide plus water vapor minus the signal representative of water vapor and minus the signal representative of carbon dioxide will yield a signal representative of carbon monoxide alone to scaling amplifier 68. Signals from scaling amplifier 68 is processed further and fed to carbon monoxide display 16 as a more accurate determination of the carbon monoxide present in the gas sample being tested.

The foregoing embodiment discloses an apparatus and a method for removing measurement errors due to water vapor and carbon dioxide. However, simplification of the disclosed apparatus is easily achieved by removal of the sensor and associated circuitry for the measurement of water vapor. By deleting optical filter 32, solid state sensor 30, amplifier 80, filter 88, demodulator 92, filter 96, summing amplifier 100, $H_2O$ control 112, $H_2O/CO_2$ control 102, and linearization circuit 138, a circuit is disclosed for removing the effects of small amounts of water vapor or carbon dioxide. If the amount of water vapor increase above a level of approximately 3% or carbon dioxide increases above a level of approximately 7%, linearization circuit 138 is necessary and must be inserted in its position illustrated in FIG. 4. A correction circuit comprising optical filter 33, solid state sensor 31, amplifier 82, chop frequency band pass filter 118, demodulator 122, filter 126, summing amplifier 130, linearlization circuit 138 and $CO_2$ control 142 in conjunction with the circuitry associated with pneumatic detector 14 will yield a system that will correct for either carbon dioxide error or water vapor error provided that either carbon dioxide or water vapor and not both is present in the sample gas stream to be analyzed.

In the alternative, optical filter 32 with sensor 30, amplifier 80, chop frequency band pass filter 88, demodulator 92, filter 96, summing amplifier 100, and $H_2O$ control 112 may be used to remove the error of water vapor in the sample gas stream when used in conjunction with pneumatic detector 14 and its associated circuitry with summing circuit 64.

While a preferred embodiment has been shown by way of illustration, it is not to be construed as a limitation on the present invention, the present invention only being limited by the claims contained herein.

What is claimed is:

1. In a non-dispersive infrared analyzer having a pneumatic detector measuring the concentration of a preselected component gas by infrared energy absorption and producing a first signal representing component concentration, apparatus for negating the measurement effects of interferent gases comprising:

response means responsive to infrared energy for detecting the infrared energy absorbed by an interferent gas which absorbs infrared energy in the bandwidth of said preselected component gas and producing a second signal in response thereto;

filter means associated with said response means for permitting passage of an infrared bandwidth absorbed by said interferent gases while rejecting infrared bandwidths absorbed by said preselected component gas;

rectifier means connected to said response means for receiving said second signal and producing a substantially rectified third signal;

scaling means connected to said rectifier means for receiving said third signal and scaling said third signal to be compatible with said first signal; and combining means connected to said scaling means and said pneumatic gas analyzer for combining said scaled third signal and said first signal and producing an output representative of said preselected component gas.

2. The apparatus according to claim 1 wherein said response means comprises a pyroelectric sensor.

3. The apparatus according to claim 1 wherein said response means comprises a black body detector.

4. The apparatus of claim 2 or 3 wherein said filter means comprises an interference filter on a quartz substrate responsive to a bandwidth of wavelengths having its center wavelength at 2.7 microns.

5. The apparatus of claims 2 or 3 wherein said filter means comprises an interference filter on a quartz substrate responsive to a bandwidth of wavelengths having its center wavelength at 2.6 microns.

6. The apparatus according to claims 2 or 3 wherein said rectifier means comprises a synchronous rectifier.

7. A method for increasing accuracy in a system having a non-dispersive infrared analyzer with a pneumatic detector for measuring the concentration of a preselected component gas by infrared energy absorption and producing a first signal representing component concentration, said method comprising the steps of:

permitting passage of an infrared bandwidth absorbed by an interferent gas to be incident upon a detector while rejecting infrared bandwidths absorbed by said preselected component gas;

detecting the infrared energy absorbed by said interferent gas which absorbs infrared heat energy in the bandwidth of said preselected component gas and producing a second signal in response thereto;

receiving said second signal and producing a substantially rectified third signal;

receiving said third signal and scaling said third signal to be compatible with said first signal; and combining said third signal and said first signal to provide an output representative of said preselected component gas.

8. The method of claim 7 including the additional steps of detecting the infrared energy absorbed by a second interferent gas which absorbs infrared energy in the bandwidth of said preselected component gas and producing a fourth signal in response thereto;

permitting passage of an infrared bandwidth absorbed by said second interferent gas while rejecting infrared bandwidths absorbed by said preselected component gas;

receiving said fourth signal and producing a substantially rectified fifth signal;

receiving said fifth signal and scaling said fifth signal to be compatible with said first signal; and combining said fifth signal with said scaled third signal and said first signal and producing an output representative of said preselected component gas.

9. In a nondispersive infrared analyzer for measuring the quantity of carbon monoxide with spectrally interferring component gases, an apparatus for negating effects of interferent gases comprising:

first means for measuring said quantity of said carbon monoxide with said effects of said interferent gases and producing a first output representative thereof;

solid state detector for measuring said effects of said interferent gases and producing a second output representative thereof; and second means for combining said first output and said second output and producing a signal representative of said quantity of said carbon monoxide.

10. The apparatus of claim 9 wherein said second means comprises a process circuit including a rectifier, and scaler associated therewith.

11. The apparatus of claim 10 wherein said solid state detector comprises a pyroelectric sensor.

12. The apparatus of claim 10 wherein said solid state detector comprises a black body detector.

13. The apparatus of claim 10 wherein said process circuit also includes a linearization circuit.

14. In a dual-beam infrared radiant energy analyzer of the type having a reference and sample radiation path and a pneumatic detector sensitized to detect radiation absorbed by gas of interest in a first selected wavelength region and producing a detector signal proportional to the concentration of said gas of interest plus any interferent gas present in the sample having an absorption band in said first selected wavelength region, the improvement comprising:

filter means disposed in said sample radiation path, said filter means having a narrow infrared radiant energy band pass in a second wavelength region where said interferent gas also has an absorption band and said constituent gas has no appreciable absorption band;

solid state detector means disposed adjacent said filter means and producing an electrical signal proportional to the concentration of said interferent gas; and circuit means connected to said pneumatic detector and to said solid state detector means for producing an output signal proportional to said constituent gas.

15. The infrared radiant energy analyzer according to claim 14 further comprising:

second filter means disposed in said sample radiation path, said second filter means having a narrow, infrared radiant energy band pass in a third region where a second interferent gas has an absorption band and said constituent gas has no appreciable absorption band;

second solid state detector means disposed adjacent said second filter means and producing a second electrical signal proportional to the concentration of said second interferent gas; and means for connecting said second solid state detector means to said circuit means whereby said circuit means produces an output signal proportional to said constituent gas.

16. The infrared radiant energy analyzer according to claim 15 wherein said first filter means has a bandwidth with a center point of 2.694 microns and a bandwidth of 0.04 microns.

17. The infrared radiant energy analyzer according to claim 16 wherein said second filter means has a bandwidth having a center point of 2.6 microns with a bandwidth of 0.03 microns.

* * * * *